United States Patent [19]

Tsuboi et al.

[11] Patent Number: 5,389,648
[45] Date of Patent: Feb. 14, 1995

[54] INSECTICIDAL PYRAZOLINES

[75] Inventors: Shin-ichi Tsuboi; Katsuaki Wada, both of Oyama; Fritz Maurer, Wuppertal; Yumi Hattori; Shinzaburo Sone, both of Oyama, all of Japan

[73] Assignee: Nihon Bayer Agrochem K.K., Tokyo, Japan

[21] Appl. No.: 223,369

[22] Filed: Apr. 4, 1994

Related U.S. Application Data

[63] Continuation of Ser. No. 957,324, Oct. 6, 1992, abandoned.

[30] Foreign Application Priority Data

Oct. 18, 1991 [JP] Japan ................... 3-297773

[51] Int. Cl.⁶ ............... C07D 401/14; C07D 405/14; A61K 31/44
[52] U.S. Cl. ................... 514/333; 514/338; 514/341; 546/256; 546/270; 546/279
[58] Field of Search ............ 514/333, 338, 341; 546/256, 270, 279

[56] References Cited

U.S. PATENT DOCUMENTS

| | | | |
|---|---|---|---|
| 4,070,365 | 1/1978 | van Daalen et al. | 548/379 |
| 4,140,792 | 2/1979 | Sirrenberg et al. | 548/379 |
| 4,156,007 | 5/1979 | van Daalen et al. | 424/273 |
| 4,174,393 | 11/1979 | van Daalen et al. | 548/379 |
| 4,572,914 | 2/1986 | van Hes et al. | 548/379 |

FOREIGN PATENT DOCUMENTS

| | | |
|---|---|---|
| 0058424 | 2/1982 | European Pat. Off. |
| 0227055 | 12/1986 | European Pat. Off. |
| 2304584 | 8/1973 | Germany |
| 7301203 | 1/1973 | Netherlands |
| 2166137 | 10/1985 | United Kingdom |
| 7900858 | 3/1979 | WIPO |

*Primary Examiner*—Marianne M. Cintins
*Assistant Examiner*—Phyllis G. Spivack
*Attorney, Agent, or Firm*—Sprung Horn Kramer & Woods

[57] ABSTRACT

Novel insecticidal pyrazolines of the formula

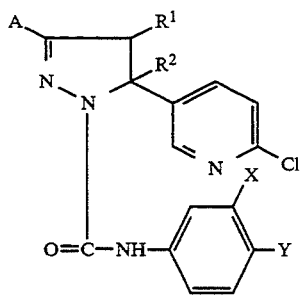

wherein
R¹ and R² represent hydrogen, $C_{1-4}$ alkyl, or unsubstituted or halogen substituted phenyl,
A represents optionally substituted phenyl or halogen-substituted 3-pyridyl, and
X and Y individually represent hydrogen, halogen, $C_{1-4}$ alkyl, halogeno-$C_{1-4}$ alkyl, halogeno-$C_{1-4}$ alkoxy or halogeno-$C_{1-4}$ alkylthio, or X and Y together form haloalkylenedioxy, with the proviso that X and Y do not simultaneously represent hydrogen, and other provisos as well.

8 Claims, No Drawings

INSECTICIDAL PYRAZOLINES

This application is a continuation of application Ser. No. 07/957,324, filed Oct. 6, 1992, now abandoned.

The present invention relates to novel pyrazolines, to a process for their preparation, to their use as insecticides, as well as to novel intermediates for their preparation and to a process for the preparation of those intermediates.

It has already been disclosed that certain pyrazolines are useful as insecticides (see, Japanese Laid-open patent application No. 87028/1973, which is an equivalent of DE-A 2,304,586 and of U.S. Pat. Nos. 3,991,073; 4,010,271 and 4,095,026). There have now been found novel pyrazolines of the formula (I)

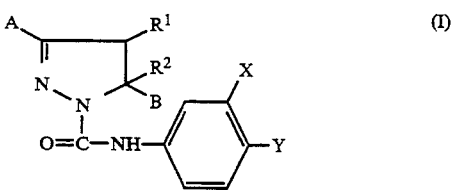

wherein
$R^1$ and $R^2$ represent hydrogen, $C_{1-4}$ alkyl, or unsubstituted or halogen-substituted phenyl,
A represents phenyl which may be substituted by at least one member selected from the group consisting of halogen, $C_{1-4}$ alkyl, $C_{1-4}$ alkoxy, halogen-$C_{1-4}$ alkyl, halogen-$C_{1-4}$ alkoxy, nitro, haloalkylenedioxy, unsubstituted or halogen-substituted phenyl, and unsubstituted or halogen-substituted phenoxy, or A represents halogen-substituted 3-pyridyl,
B represents phenyl which may be substituted by halogen, or B represents halogen-substituted or $C_{1-4}$alkoxy-substituted 3-pyridyl, and
X and Y individually represent hydrogen, halogen, $C_{1-4}$alkyl, halogeno-$C_{1-4}$alkyl, halogeno-$C_{1-4}$alkoxy or halogeno-$C_{1-4}$alkylthio, or X and Y together form a haloalkylenedioxy group,
with the provisos that:
X and Y do not simultaneously represent hydrogen, at least one of A and B represents halogen-substituted pyridyl, and when $R^1$ and $R^2$ simultaneously represent hydrogen, then A represents phenyl substituted by at least one member selected from the group consisting of halogeno-$C_{1-4}$alkoxy, nitro, halomethylenedioxy, unsubstituted or halogen-substituted phenyl and unsubstituted or halogen-substituted phenoxy, or at least one of X and Y represents halogeno-$C_{1-4}$alkoxy or halogeno-$C_{1-4}$alkylthio, or X and Y together form haloalkylenedioxy The pyrazolines of the formula (I) are obtained when
a) pyrazolines of the formula (II)

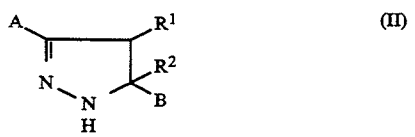

are reacted with phenyl isocyanates of the formula (III)

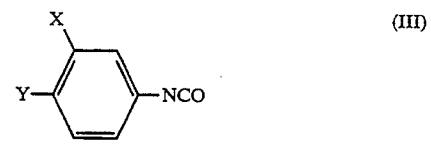

in the presence of inert solvents.

The novel pyrazolines of the formula (I) exhibit powerful insecticidal properties.

Surprisingly, pyrazolines according to the invention exhibit a substantially greater insecticidal activity than those known from the prior art of the above-mentioned Japanese Laid-open patent application.

In the formulas (I), (II) and (III), halogen includes fluorine, chlorine, bromine and iodine preferably fluorine, chlorine and bromine especially fluorine and chlorine.

The $C_{1-4}$ alkyl groups and $C_{1-4}$ alkyl moieties contained in $C_{1-4}$ alkoxy groups, halogeno-$C_{1-4}$ alkyl groups, halogeno-$C_{1-4}$ alkoxy groups and halogeno-$C_{1-4}$ alkylthio groups, include methyl, ethyl, n-propyl, isopropyl, and n-(or iso-, sec- or tert-)butyl groups, preferably methyl, ethyl, n-propyl and isopropyl groups.

Among the pyrazolines according to the invention of the formula (I), preferred compounds are those in which
$R^1$ and $R^2$ represent hydrogen, methyl, ethyl, isopropyl, tert-butyl or unsubstituted or chlorine-substituted phenyl,
A represents phenyl which may be substituted by at least one member selected from the group consisting of fluorine, chlorine, bromine, $C_{1-4}$ alkyl, $C_{1-2}$alkoxy, fluoro- and/or chloro-$C_{1-2}$alkyl, fluoro- and/or chloro-$C_{1-2}$alkoxy, nitro, difluoromethylenedioxy, unsubstituted or fluoro-and/or chloro-substituted phenyl, and unsubstituted or chloro- and/or bromo-substituted phenoxy, or A represents fluoro-, chloro- or bromo-substituted 3-pyridyl,
B represents phenyl which may be substituted by fluorine, chlorine and bromine, or B represents fluoro-, chloro-, bromo- or methoxy-substituted pyridyl, and
X and Y represent hydrogen, chlorine, fluoro- and/or chloro-$C_{1-2}$alkyl, fluoro- and/or chloro-$C_{1-2}$alkoxy, or fluoro- and/or chloro-$C_{1-2}$alkylthio, or X and Y together form difluoromethylenedioxy or tetrafluoroethylenedioxy,
with the stated provisos.

Very particularly preferred pyrazolines of the formula (I) are those in which $R^1$ and $R^2$ represents hydrogen, methyl, ethyl, isopropyl, tert-butyl, phenyl or 4-chorophenyl.
A represents phenyl which may be substituted by at least one member selected from the group consisting of fluorine, chlorine, methyl, tert-butyl, methoxy, trifluoromethyl, difluoromethoxy, trifluoromethoxy, nitro, difluoromethylenedioxy, unsubstituted or chloro-substituted phenyl, and unsubstituted or chloro- and/or bromo-substituted phenoxy, or A represents chlorine- or bromine-substituted 3-pyridyl,
B represents fluoro- or chloro-substituted phenyl, or chloro- or bromo-substituted 3-pyridyl,
X represents hydrogen or chlorine, and Y represents chlorine, difluoromethyl, trifluoromethyl, trifluoromethoxy or trifluoromethylthio, or X and Y together form a difluoromethylenedioxy group or a tetrafluoroethylenedioxy group, with the stated provisos.

In addition to the compounds disclosed in the Preparation Examples the following compounds of general formula I are noted:

TABLE 1

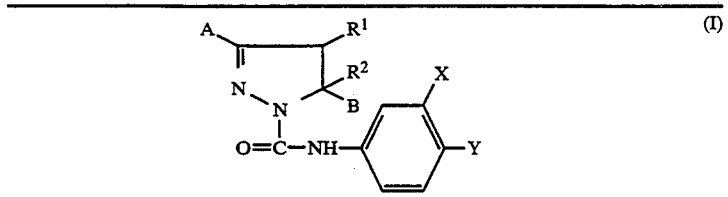

(I)

| A | B | X | Y | R$^1$ | R$^2$ |
|---|---|---|---|---|---|
| phenyl | 6-Cl-3-pyridyl | H | OCF$_3$ | H | H |
| phenyl | 6-Cl-3-pyridyl | Cl | OCF$_3$ | H | H |
| 4-F-phenyl | 6-Cl-3-pyridyl | H | OCF$_3$ | H | H |
| 4-F-phenyl | 6-Cl-3-pyridyl | Cl | OCF$_3$ | H | H |
| 4-F-phenyl | 6-Cl-3-pyridyl | OCF$_2$O | | H | H |
| 4-F-phenyl | 6-Cl-3-pyridyl | OC$_2$F$_4$O | | H | H |
| 4-F-phenyl | 6-Cl-3-pyridyl | H | SCF$_3$ | H | H |
| 4-F-phenyl | 6-Cl-3-pyridyl | Cl | SCF$_3$ | H | H |
| 4-Cl-phenyl | 6-Cl-3-pyridyl | H | OCF$_3$ | H | H |
| 4-Cl-phenyl | 6-Cl-3-pyridyl | Cl | OCF$_3$ | H | H |
| 4-Cl-phenyl | 6-Cl-3-pyridyl | OCF$_2$O | | H | H |
| 4-Cl-phenyl | 6-Cl-3-pyridyl | OC$_2$F$_4$O | | H | H |
| 4-Cl-phenyl | 6-Cl-3-pyridyl | H | SCF$_3$ | H | H |
| 4-Cl-phenyl | 6-Cl-3-pyridyl | Cl | SCF$_3$ | H | H |
| 3,4-Cl$_2$-phenyl | 6-Cl-3-pyridyl | H | OCF$_3$ | H | H |
| 3,4-Cl$_2$-phenyl | 6-Cl-3-pyridyl | Cl | OCF$_3$ | H | H |
| 4-OCHF$_2$-phenyl | 6-Cl-3-pyridyl | H | Cl | H | H |
| 4-OCHF$_2$-phenyl | 6-Cl-3-pyridyl | H | CF$_3$ | H | H |
| 4-OCHF$_2$-phenyl | 6-Cl-3-pyridyl | Cl | CF$_3$ | H | H |
| 4-OCHF$_2$-phenyl | 6-Cl-3-pyridyl | H | CHF$_2$ | H | H |
| 4-OCHF$_2$-phenyl | 6-Cl-3-pyridyl | H | OCF$_3$ | H | H |
| 4-OCHF$_2$-phenyl | 6-Cl-3-pyridyl | Cl | OCF$_3$ | H | H |
| 4-OCF$_3$-phenyl | 6-Cl-3-pyridyl | H | Cl | H | H |
| 4-OCF$_3$-phenyl | 6-Cl-3-pyridyl | H | CF$_3$ | H | H |
| 4-OCF$_3$-phenyl | 6-Cl-3-pyridyl | Cl | CF$_3$ | H | H |
| 4-OCF$_3$-phenyl | 6-Cl-3-pyridyl | H | CHF$_2$ | H | H |
| 4-OCF$_3$-phenyl | 6-Cl-3-pyridyl | H | OCF$_3$ | H | H |
| 4-OCF$_3$-phenyl | 6-Cl-3-pyridyl | Cl | OCF$_3$ | H | H |
| 4-NO$_2$-phenyl | 6-Cl-3-pyridyl | H | CF$_3$ | H | H |
| 4-CH$_3$-phenyl | 6-Cl-3-pyridyl | H | OCF$_3$ | H | H |
| 4-tert-C$_4$H$_9$-phenyl | 6-Cl-3-pyridyl | H | OCF$_3$ | H | H |
| 4-OCH$_3$-phenyl | 6-Cl-3-pyridyl | H | OCF$_3$ | H | H |
| 4-biphenylyl | 6-Cl-3-pyridyl | H | OCF$_3$ | H | H |
| 4'-Cl-4-biphenyl | 6-Cl-3-pyridyl | H | OCF$_3$ | H | H |
| 4-phenoxyphenyl | 6-Cl-3-pyridyl | H | OCF$_3$ | H | H |
| 4'-Cl-4-phenoxyphenyl | 6-Cl-3-pyridyl | H | OCF$_3$ | H | H |
| 4'-Br-4-phenoxyphenyl | 6-Cl-3-pyridyl | H | OCF$_3$ | H | H |
| 6-Cl-3-pyridyl | 6-Cl-3-pyridyl | H | OCF$_3$ | H | H |
| 6-Cl-3-pyridyl | 6-Cl-3-pyridyl | Cl | OCF$_3$ | H | H |
| 6-Cl-3-pyridyl | 6-Cl-3-pyridyl | H | SCF$_3$ | H | H |
| 6-Cl-3-pyridyl | 6-Cl-3-pyridyl | Cl | SCF$_3$ | H | H |
| 4-F-phenyl | 5,6-Cl$_2$-3-pyridyl | H | OCF$_3$ | H | H |
| 4-Cl-phenyl | 5,6-Cl$_2$-3-pyridyl | H | OCF$_3$ | H | H |
| 4-OCHF$_2$-phenyl | 5,6-Cl$_2$-3-pyridyl | H | CF$_3$ | H | H |
| 4-OCF$_3$-phenyl | 5,6-Cl$_2$-3-pyridyl | H | CF$_3$ | H | H |
| 4-F-phenyl | 5-Br-3-pyridyl | H | OCF$_3$ | H | H |
| 4-Cl-phenyl | 2-Cl-3-pyridyl | H | OCF$_3$ | H | H |
| 4-OCHF$_2$-phenyl | 6-OCH$_3$-3-pyridyl | H | CF$_3$ | H | H |
| 4-OCHF$_2$-phenyl | 6-OCH$_3$-3-pyridyl | H | OCF$_3$ | H | H |
| 4-OCF$_3$-phenyl | 2-Cl-4-pyridyl | H | Cl | H | H |
| 4-OCF$_3$-phenyl | 2-Cl-4-pyridyl | H | CF$_3$ | H | H |
| 4-OCF$_3$-phenyl | 2-Cl-4-pyridyl | H | OCF$_3$ | H | H |
| 6-Cl-3-pyridyl | phenyl | H | OCF$_3$ | H | H |
| 6-Cl-3-pyridyl | phenyl | Cl | OCF$_3$ | H | H |
| 6-Cl-3-pyridyl | 4-F-phenyl | H | OCF$_3$ | H | H |
| 6-Cl-3-pyridyl | 4-F-phenyl | Cl | OCF$_3$ | H | H |
| 6-Cl-3-pyridyl | 4-Cl-phenyl | H | OCF$_3$ | H | H |
| 6-Cl-3-pyridyl | 4-Cl-phenyl | Cl | OCF$_3$ | H | H |
| 4-F-phenyl | 6-Cl-3-pyridyl | H | Cl | CH$_3$ | H |
| 4-F-phenyl | 6-Cl-3-pyridyl | H | CF$_3$ | CH$_3$ | H |
| 4-F-phenyl | 6-Cl-3-pyridyl | Cl | CF$_3$ | CH$_3$ | H |
| 4-F-phenyl | 6-Cl-3-pyridyl | H | OCF$_3$ | CH$_3$ | H |
| 4-F-phenyl | 6-Cl-3-pyridyl | Cl | OCF$_3$ | CH$_3$ | H |
| 4-F-phenyl | 6-Cl-3-pyridyl | H | SCF$_3$ | CH$_3$ | H |
| 4-F-phenyl | 6-Cl-3-pyridyl | Cl | SCF$_3$ | CH$_3$ | H |
| 4-Cl-phenyl | 6-Cl-3-pyridyl | H | Cl | CH$_3$ | H |

TABLE 1-continued

Structure (I):
A–C(=N–N(–C(=O)–NH–Ar)–CR²B)–R¹ pyrazoline, where Ar is a phenyl bearing X (meta) and Y (para).

| A | B | X | Y | R¹ | R² |
|---|---|---|---|---|---|
| 4-Cl-phenyl | 6-Cl-3-pyridyl | H | CF₃ | CH₃ | H |
| 4-Cl-phenyl | 6-Cl-3-pyridyl | Cl | CF₃ | CH₃ | H |
| 4-Cl-phenyl | 6-Cl-3-pyridyl | H | OCF₃ | CH₃ | H |
| 4-Cl-phenyl | 6-Cl-3-pyridyl | Cl | OCF₃ | CH₃ | H |
| 4-OCHF₂-phenyl | 6-Cl-3-pyridyl | H | Cl | CH₃ | H |
| 4-OCHF₂-phenyl | 6-Cl-3-pyridyl | H | CF₃ | CH₃ | H |
| 4-OCHF₂-phenyl | 6-Cl-3-pyridyl | Cl | CF₃ | CH₃ | H |
| 4-OCHF₂-phenyl | 6-Cl-3-pyridyl | Cl | OCF₃ | CH₃ | H |
| 4-OCHF₂-phenyl | 6-Cl-3-pyridyl | Cl | OCF₃ | CH₃ | H |
| 4-OCF₃-phenyl | 6-Cl-3-pyridyl | H | Cl | CH₃ | H |
| 4-OCF₃-phenyl | 6-Cl-3-pyridyl | H | CF₃ | CH₃ | H |
| 4-OCF₃-phenyl | 6-Cl-3-pyridyl | Cl | CF₃ | CH₃ | H |
| 4-OCF₃-phenyl | 6-Cl-3-pyridyl | H | OCF₃ | CH₃ | H |
| 4-OCF₃-phenyl | 6-Cl-3-pyridyl | Cl | OCF₃ | CH₃ | H |
| 4-F-phenyl | 6-Cl-3-pyridyl | H | Cl | C₂H₅ | H |
| 4-F-phenyl | 6-Cl-3-pyridyl | H | CF₃ | C₂H₅ | H |
| 4-F-phenyl | 6-Cl-3-pyridyl | Cl | CF₃ | C₂H₅ | H |
| 4-F-phenyl | 6-Cl-3-pyridyl | H | OCF₃ | C₂H₅ | H |
| 4-F-phenyl | 6-Cl-3-pyridyl | Cl | OCF₃ | C₂H₅ | H |
| 4-Cl-phenyl | 6-Cl-3-pyridyl | H | Cl | C₂H₅ | H |
| 4-Cl-phenyl | 6-Cl-3-pyridyl | H | CF₃ | C₂H₅ | H |
| 4-Cl-phenyl | 6-Cl-3-pyridyl | Cl | CF₃ | C₂H₅ | H |
| 4-Cl-phenyl | 6-Cl-3-pyridyl | H | OCF₃ | C₂H₅ | H |
| 4-Cl-phenyl | 6-Cl-3-pyridyl | Cl | OCF₃ | C₂H₅ | H |
| 4-OCHF₂-phenyl | 6-Cl-3-pyridyl | H | Cl | C₂H₅ | H |
| 4-OCHF₂-phenyl | 6-Cl-3-pyridyl | H | CF₃ | C₂H₅ | H |
| 4-OCHF₂-phenyl | 6-Cl-3-pyridyl | Cl | CF₃ | C₂H₅ | H |
| 4-OCHF₂-phenyl | 6-Cl-3-pyridyl | H | OCF₃ | C₂H₅ | H |
| 4-OCHF₂-phenyl | 6-Cl-3-pyridyl | Cl | OCF₃ | C₂H₅ | H |
| 4-OCHF₂-phenyl | 6-Cl-3-pyridyl | Cl | SCF₃ | C₂H₅ | H |
| 4-OCF₃-phenyl | 6-Cl-3-pyridyl | H | Cl | C₂H₅ | H |
| 4-OCF₃-phenyl | 6-Cl-3-pyridyl | H | CF₃ | C₂H₅ | H |
| 4-OCF₃-phenyl | 6-Cl-3-pyridyl | Cl | CF₃ | C₂H₅ | H |
| 4-OCF₃-phenyl | 6-Cl-3-pyridyl | H | OCF₃ | C₂H₅ | H |
| 4-OCF₃-phenyl | 6-Cl-3-pyridyl | Cl | OCF₃ | C₂H₅ | H |
| 4-F-phenyl | 6-Cl-3-pyridyl | H | Cl | C₃H₇-iso | H |
| 4-F-phenyl | 6-Cl-3-pyridyl | H | CF₃ | C₃H₇-iso | H |
| 4-F-phenyl | 6-Cl-3-pyridyl | Cl | CF₃ | C₃H₇-iso | H |
| 4-F-phenyl | 6-Cl-3-pyridyl | H | OCF₃ | C₃H₇-iso | H |
| 4-F-phenyl | 6-Cl-3-pyridyl | Cl | OCF₃ | C₃H₇-iso | H |
| 4-Cl-phenyl | 6-Cl-3-pyridyl | H | Cl | C₃H₇-iso | H |
| 4-Cl-phenyl | 6-Cl-3-pyridyl | H | CF₃ | C₃H₇-iso | H |
| 4-Cl-phenyl | 6-Cl-3-pyridyl | Cl | CF₃ | C₃H₇-iso | H |
| 4-Cl-phenyl | 6-Cl-3-pyridyl | H | OCF₃ | C₃H₇-iso | H |
| 4-Cl-phenyl | 6-Cl-3-pyridyl | Cl | OCF₃ | C₃H₇-iso | H |
| 4-OCHF₂-phenyl | 6-Cl-3-pyridyl | H | Cl | C₃H₇-iso | H |
| 4-OCHF₂-phenyl | 6-Cl-3-pyridyl | H | CF₃ | CF₃H₇-iso | H |
| 4-OCHF₂-phenyl | 6-Cl-3-pyridyl | Cl | CF₃ | CF₃H₇-iso | H |
| 4-OCHF₂-phenyl | 6-Cl-3-pyridyl | H | OCF₃ | CF₃H₇-iso | H |
| 4-OCHF₂-phenyl | 6-Cl-3-pyridyl | Cl | OCF₃ | CF₃H₇-iso | H |
| 4-OCF₃-phenyl | 6-Cl-3-pyridyl | H | Cl | CF₃H₇-iso | H |
| 4-OCF₃-phenyl | 6-Cl-3-pyridyl | H | CF₃ | CF₃H₇-iso | H |
| 4-OCF₃-phenyl | 6-Cl-3-pyridyl | Cl | CF₃ | CF₃H₇-iso | H |
| 4-OCF₃-phenyl | 6-Cl-3-pyridyl | H | OCF₃ | CF₃H₇-iso | H |
| 4-OCF₃-phenyl | 6-Cl-3-pyridyl | Cl | OCF₃ | CF₃H₇-iso | H |
| 4-Cl-phenyl | 6-Cl-3-pyridyl | H | Cl | C₄H₉-tert | H |
| 4-Cl-phenyl | 6-Cl-3-pyridyl | H | CF₃ | C₄H₉-tert | H |
| 4-Cl-phenyl | 6-Cl-3-pyridyl | Cl | CF₃ | C₄H₉-tert | H |
| 4-Cl-phenyl | 6-Cl-3-pyridyl | H | OCF₃ | C₄H₉-tert | H |
| 4-Cl-phenyl | 6-Cl-3-pyridyl | Cl | OCF₃ | C₄H₉-tert | H |
| 4-Cl-phenyl | 6-Cl-3-pyridyl | H | Cl | phenyl | H |
| 4-Cl-phenyl | 6-Cl-3-pyridyl | H | CF₃ | phenyl | H |
| 4-Cl-phenyl | 6-Cl-3-pyridyl | Cl | CF₃ | phenyl | H |
| 4-Cl-phenyl | 6-Cl-3-pyridyl | H | OCF₃ | phenyl | H |
| 4-Cl-phenyl | 6-Cl-3-pyridyl | Cl | OCF₃ | phenyl | H |
| 4-Cl-phenyl | 6-Cl-3-pyridyl | Cl | OCF₃ | 4-Cl-phenyl | H |
| 4-F-phenyl | 6-Cl-3-pyridyl | H | Cl | H | CH₃ |
| 4-F-phenyl | 6-Cl-3-pyridyl | H | CF₃ | H | CH₃ |
| 4-F-phenyl | 6-Cl-3-pyridyl | Cl | CF₃ | H | CH₃ |
| 4-F-phenyl | 6-Cl-3-pyridyl | H | OCF₃ | H | CH₃ |
| 4-F-phenyl | 6-Cl-3-pyridyl | Cl | OCF₃ | H | CH₃ |

TABLE 1-continued

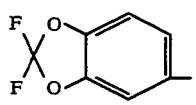

| A | B | X | Y | R¹ | R² |
|---|---|---|---|---|---|
| 4-Cl-phenyl | 6-Cl-3-pyridyl | H | Cl | H | $CH_3$ |
| 4-Cl-phenyl | 6-Cl-3-pyridyl | H | $CF_3$ | H | $CH_3$ |
| 4-Cl-phenyl | 6-Cl-3-pyridyl | Cl | $CF_3$ | H | $CH_3$ |
| 4-Cl-phenyl | 6-Cl-3-pyridyl | H | $OCF_3$ | H | $CH_3$ |
| 4-Cl-phenyl | 6-Cl-3-pyridyl | Cl | $OCF_3$ | H | $CH_3$ |
| 4-Cl-phenyl | 6-Cl-3-pyridyl | H | Cl | H | phenyl |
| 4-Cl-phenyl | 6-Cl-3-pyridyl | H | $CF_3$ | H | phenyl |
| 4-Cl-phenyl | 6-Cl-3-pyridyl | H | $OCF_3$ | H | phenyl |
| 4-Cl-phenyl | 6-Cl-3-pyridyl | H | Cl | H | 4-Cl-phenyl |
| 4-Cl-phenyl | 6-Cl-3-pyridyl | H | $CF_3$ | H | 4-Cl-phenyl |
| 4-Cl-phenyl | 6-Cl-3-pyridyl | H | $OCF_3$ | H | 4-Cl-phenyl |
| 4-$CF_3$-phenyl | 6-Cl-3-pyridyl | H | $OCF_3$ | H | H |
| 4-$CHF_2$-phenyl | 6-Cl-3-pyridyl | H | $OCF_3$ | H | H |
| 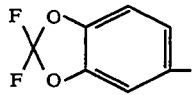 | 6-Cl-3-pyridyl | H | Cl | H | H |
| 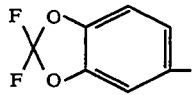 | 6-Cl-3-pyridyl | H | $CF_3$ | H | H |
| 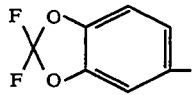 | 6-Cl-3-pyridyl | H | $OCF_3$ | H | H |

If, for example, 3-phenyl-5-(6-chloro-3-pyridyl)-2-pyrazoline and 4-trifluoromethoxyphenyl isocyanate are used as starting materials, the course of the reaction can be represented by the following equation:

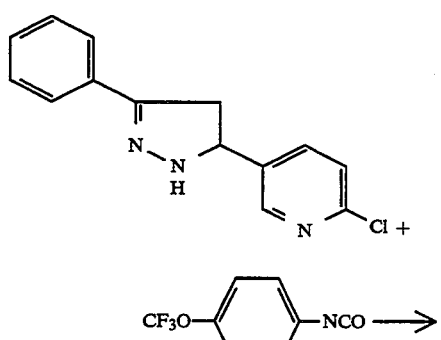

-continued

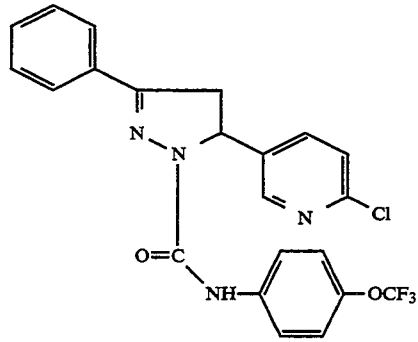

The starting material of the formula (II) can be obtained in analogy to the process described in Japanese Laid-Open Patent application No. 87028/1973, as illustrated in detail in the Example below.

The starting materials of the formula (II) are obtained when compounds of the formula (IV)

are reacted with hydrazine hydrate, in the presence of inert solvents.

The compounds of formula (IV) are novel and can be obtained, for instance, when compounds of the formula (V)

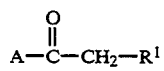

are reacted with compound of the formula (VI)

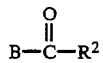

if appropriate in the presence of acid binding substances and in the presence of inert solvents, or compounds of the formula (VII)

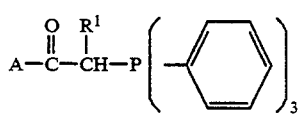

are reacted with compounds of the above mentioned formula (VI) in the presence of inert solvents.

The compounds of formulas (V) and (IV) are compounds known in the field of organic chemistry.

The compounds of formula (VII) are novel compounds, and can be obtained, for instance, when compounds of the formula (VIII)

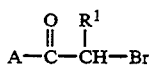

are reacted with triphenylphosphine in the presence of inert solvents, to give compounds of the formula (IX)

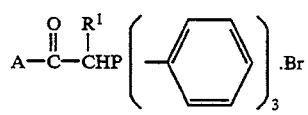

and the compounds of formula (IX) are subjected to an alkaline treatment.

The compounds represented by the formula (VIII) can be obtained by reaction of the above mentioned compounds of formula (V) with bromine.

As representative examples of the starting material of the formula (II) there may be mentioned:
3-phenyl-5-(6-chloro-3-pyridyl)-2-pyrazoline,
3-(4-fluorophenyl)-5-(6-chloro-3-pyridyl)-2-pyrazoline,
3-(4-chlorophenyl)-5-(6-chloro-3-pyridyl)-2-pyrazoline,
3-(3,4-dichlorophenyl)-5-(6-chloro-3-pyridyl)-2-pyrazoline,
3-(4-difluoromethoxyphenyl)-5-(6-chloro-3-pyridyl)-2-pyrazoline,
3-(4-trifluoromethoxyphenyl)-5-(6-chloro-3-pyridyl)-2-pyrazoline,
3-(4-nitrophenyl)-5-(6-chloro-3-pyridyl)-2-pyrazoline,
3-(4-methylphenyl)-5-(6-chloro-3-pyridyl)-2-pyrazoline,
3-(4-tert-butylphenyl)-5-(6-chloro-3-pyridyl)-2-pyrazoline,
3-(4-methoxyphenyl)-5-(6-chloro-3-pyridyl)-2-pyrazoline,
3-(4-biphenylyl)-5-(6-chloro-3-pyridyl)-2-pyrazoline,
3-(4'-chloro-4-biphenylyl)-5-(6-chloro-3-pyridyl)-2-pyrazoline,
3-(4-phenoxyphenyl)-5-(6-chloro-3-pyridyl)-2-pyrazoline,
3-(4'-chloro-4-phenoxyphenyl)-5-(6-chloro-3-pyridyl)-2-pyrazoline,
3-(4'-bromo-4-phenoxyphenyl)-5-(6-chloro-3-pyridyl)-2-pyrazoline,
3,5-bis-(6-chloro-3-pyridyl)-2-pyrazoline,
3-(6-chloro-3-pyridyl)-5-phenyl-2-pyrazoline,
3-(6-chloro-3-pyridyl)-5-(4-fluorophenyl)-2-pyrazoline,
3-(6-chloro-3-pyridyl)-5-(4-chlorophenyl)-2-pyrazoline,
3-(4-fluorophenyl)-5-(6-chloro-3-pyridyl)-4-methyl-2-pyrazoline,
3-(4-chlorophenyl)-5-(6-chloro-3-pyridyl)-4-methyl-2-pyrazoline,
3-(4-difluoromethoxyphenyl)-5-(6-chloro-3-pyridyl)-4-methyl-2-pyrazoline,
3-(4-trifluoromethoxyphenyl)-5-(6-chloro-3-pyridyl)-4-methyl-2-pyrazoline,
3-(4-fluorophenyl)-5-(6-chloro-3-pyridyl)-4-ethyl-2-pyrazoline,
3-(4-chlorophenyl)-5-(6-chloro-3-pyridyl)-4-ethyl-2-pyrazoline,
3-(4-difluoromethoxyphenyl)-5-(6-chloro-3-pyridyl)-4-ethyl-2-pyrazoline,
3-(4-trifluoromethoxyphenyl)-5-(6-chloro-3-pyridyl)-4-ethyl-2-pyrazoline,
3-(4-fluorophenyl)-5-(6-chloro-3-pyridyl)-4-isopropyl-2-pyrazoline,
3-(4-chlorophenyl)-5-(6-chloro-3-pyridyl)-4-isopropyl-2-pyrazoline,
3-(4-difluoromethoxyphenyl)-5-(6-chloro-3-pyridyl)-4-isopropyl-2-pyrazoline,
3-(4-trifluoromethoxyphenyl)-5-(6-chloro-3-pyridyl)-4-isopropyl-2-pyrazoline,
3-(4-chlorophenyl)-5-(6-chloro-3-pyridyl)-4-tret-butyl-2-pyrazoline,
3-(4-chlorophenyl)-5-(6-chloro-3-pyridyl)-4-phenyl-2-pyrazoline,
3,4-bis-(4-chlorophenyl)-5-(6-chloro-3-pyridyl)-2-pyrazoline,
3-(4-fluorophenyl)-5-(6-chloro-3-pyridyl)-5-methyl-2-pyrazoline,
3-(4-chlorophenyl)-5-(6-chloro-3-pyridyl)-5-methyl-2-pyrazoline,
3-(4-chlorophenyl)-5-(6-chloro-3-pyridyl)-5-phenyl-2-pyrazoline, and
3,5-bis-(4-chlorophenyl)-5-(6-chloro-3-pyridyl)-2-pyrazoline.

The starting materials of formula II are well known phenyl isocyanates, representative examples of which include:
4-trifluoromethoxyphenyl isocyanate,
3-chloro-4-trifluoromethoxylphenyl isocyanate,
3,4-difluoromethylenedioxyphenyl isocyanate,
3,4-tetrafluoromethylenedioxyphenyl isocyanate,
4-trifluoromethylthiophenyl isocyanate,
4-chlorophenyl isocyanate,
4-trifluoromethylphenyl isocyanate, and
4-difluoromethylphenyl isocyanate.

In carrying out the process mentioned above, any inert solvent can be used as suitable diluent.

Examples of such diluents are water; aliphatic, cycloaliphatic and aromatic, optionally chlorinated, hydrocarbons such as pentane, hexane, cyclohexane, petroleum ether, ligroin, benzene, toluene, xylene, dichloromethane, chloroform, carbon tetrachloride, ethylene chloride, chlorobenzene, dichlorobenzene, and the like; ethers such as diethyl ether, methyl ethyl ether, di-iso-propyl ether, di-butyl ether, propylene oxide, dimethoxyethane (DME), dioxane, tetrahydrofurane (THF) and the like; ketones such as acetone methylethyl ketone (MEK), methyl-iso-propyl ketone, methyl-isobutyl ketone (MIBK) and the like; nitriles such as acetonitrile, propionitrile, acrylonitrile, and the like; alcohols such as methanol, ethanol, iso-propanol, butanol, ethylene glycol and the like; esters such as ethyl acetate, amyl acetate, and the like; acid amides such as dimethyl formamide, diethyl acetamide, and the like; sulfones and sulfoxides such as dimethyl sulfoxide, sulfolane and the like; and, bases, for example, such as pyridine.

In the above mentioned process a), the reaction temperature can be varied within a substantially wide range. In general, the reaction is carried out at a temperature of from about 0° C. to about 120° C., preferably from 10° C. to about 40° C.

Further, the reaction is preferably carried out under normal pressure, although it is also possible to employ a higher or reduced pressure.

When the above mentioned process a) according to the present invention is carried out, use is made, for example, of the above mentioned compound (III) in an amount from 1.0 to 1.5 mols, preferably 1 to 1.2 mols, per mol of the above mentioned compound (II), optionally in the presence of inert solvents such as acetonitrile, for example, to obtain the desired compounds of the formula (I).

The active compounds of the formula (I) are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example, Oniscus Asellus, *Armadillidium vulgare* and *Porcellio scaber;* from the class of the Diplopoda, for example, *Blaniulus guttulatus;* from the class of the Chilopoda, for example, *Geophilus carpophagus* and Scutigera spec.;

from the class of the Symphyla, for example, *Scuti gerella immaculata;* from the order of the Thysanura, for example, *Lepisma saccharina;* from the order of the Collembola, for example, *Onychiurus armatus;* from the order of the Orthoptera; for example, *Blatta orientalis, Periplaneta americana, Leucophaea maderae, Blattella germanica, Acheta domesticus,* Gryllotalpa spp., *Locusta migrato ria migratorioides, Melanoplus differentialis* and *Schistocerca gregaria;* from the order of the Dermaptera, for example, *Forficula auricularia;* from the order of the Isoptera, for example, Reticulitermes spp.;

from the order of the Anoplura, for example, *Phylloxera vastatrix*, Pemphigus spp., *Pediculus humanus corporis*, Haematopinus spp. and Linognathus spp.;

from the order of the Mallophaga, for example, Trichodectes spp. and Damalinea spp.;

from the order of the Thysanoptera, for example, *Hercinothrips femoralis* and *Thrips tabaci,* from the order of the Heteroptera, for example, Eurygaster spp., *Dysdercus intermedius, Piesma guadrata, Cimex lectularius, Rhodnius prolixus* and Triatoma spp.; from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.:

from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorr hynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Pitnus spp., *Niptus hololeucus, Gibbium psylloides,* Tribolium spp., *Tenebrio molitor,* Agriotes spp., Conoderus spp., *Melofontha melolontha, Amphimallon solstitialis* and *Costelytra zealandica;* from the order of the Hymenoptera for example, Diprion spp., Hoplocampa spp., Lasius spp., *Monomorium pharaonis* and Vespa spp.;

from the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs, and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates or aryl sulphonates, as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in customary manner appropriate for the use

When used against hygiene pests and pests of stored products, the active compounds are distinguished by an excellent residual action on wood and clay as well as good stability to alkali on limed substrates.

The preparation and use of the active compounds according to the invention can be seen from the following examples.

EXAMPLE 1

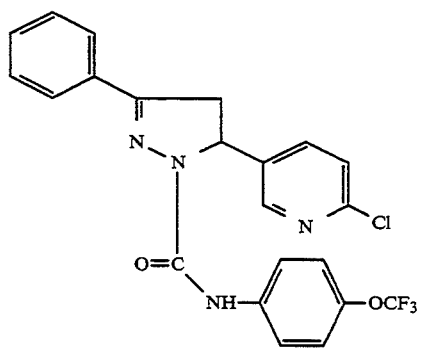

(Compound No 1)

3-phenyl-5-(6-chloro-3-pyridyl)-2-pyrazoline (2.58 g) was dissolved in 10 ml of acetonitrile. The resulting solution was admixed with 4-trifluoromethoxyphenyl isocyanate (2.03 g) at room temperature, and stirred at room temperature for 10 hours, and then the solvent was distilled off under reduced pressure. The crude product thus formed was recrystallized from ethanol to give 1-(4-trifluoromethoxyphenyl) carbomoyl-3-phenyl-5-(6-chloro-3-pyridyl)-2-pyrazoline (2.81 g). mp 145°–147° C.

EXAMPLE 2

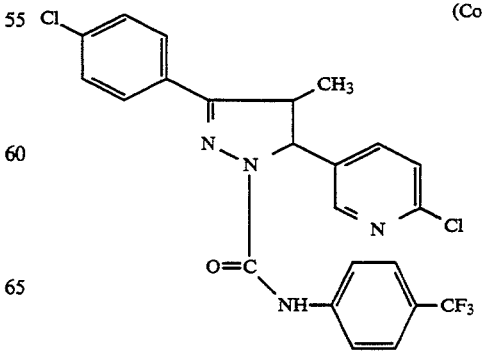

(Compound No 20)

3-(4-chlorophenyl)-4-methyl-5-(6-chloro-3-pyridyl)-2-pyrazoline (4.6 g) was dissolved in 40 ml of acetonitrile. The resulting solution was admixed with 4-trifluoromethylphenyl isocyanate (2.8 g) at room temperature, and stirred at room temperature for 18 hours, and then the solvent was distilled off under reduced pressure. The crude product thus formed was recrystallized from ethanol to give 1-(4-trifluoromethylphenyl)-carbamoyl-3-(4-chlorophenyl)-4-methyl-5-(6-chloro-3-pyridyl)-2-pyrazoline (4.8 g). mp 173°–174° C.

The following Table 2 includes the compounds of Examples 1 and 2 along with others similarly produced.

EXAMPLE 4

(synthesis of intermediate compound)

(Compound No II-8)

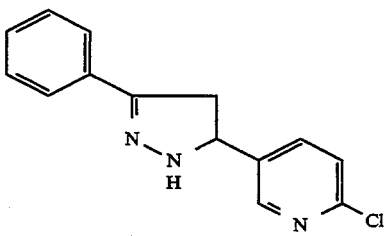

TABLE 2

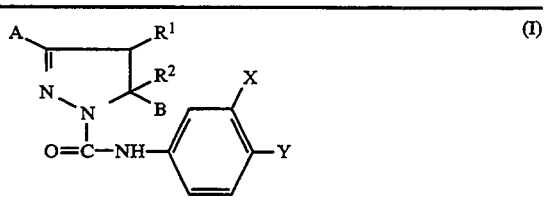

(I)

| Compound No. | A | B | X | Y | R¹ | R² | m.p., °C. |
|---|---|---|---|---|---|---|---|
| I-1 | phenyl | 6-Cl-3-pyridyl | H | OCF$_3$ | H | H | 145–147 |
| I-2 | 4-F-phenyl | 6-Cl-3-pyridyl | H | OCF$_3$ | H | H | 148–149 |
| I-3 | 4-F-phenyl | 6-Cl-3-pyridyl | Cl | OCF$_3$ | H | H | 199–200 |
| I-4 | 4-Cl-phenyl | 6-Cl-3-pyridyl | H | OCF$_3$ | H | H | 195–197 |
| I-5 | 4-Cl-phenyl | 6-Cl-3-pyridyl | Cl | OCF$_3$ | H | H | 163–166 |
| I-6 | 3,4-Cl$_2$-phenyl | 6-Cl-3-pyridyl | H | OCF$_3$ | H | H | 202–203 |
| I-7 | 4-OCHF$_2$-phenyl | 6-Cl-3-pyridyl | H | Cl | H | H | 186–193 |
| I-8 | 4-OCHF$_2$-phenyl | 6-Cl-3-pyridyl | H | CF$_3$ | H | H | 217–220 |
| I-9 | 4-OCHF$_2$-phenyl | 6-Cl-3-pyridyl | H | CHF$_2$ | H | H | 210–213 |
| I-10 | 4-OCHF$_2$-phenyl | 6-Cl-3-pyridyl | Cl | OCF$_3$ | H | H | 172–173 |
| I-11 | 4-OCF$_3$-phenyl | 6-Cl-3-pyridyl | H | Cl | H | H | 171–179 |
| I-12 | 4-OCF$_3$-phenyl | 6-Cl-3-pyridyl | H | CF$_3$ | H | H | 216–217 |
| I-13 | 4-OCF$_3$-phenyl | 6-Cl-3-pyridyl | H | CHF$_2$ | H | H | 205–207 |
| I-14 | 4-OCF$_3$-phenyl | 6-Cl-3-pyridyl | H | OCF$_3$ | H | H | 176–180 |
| I-15 | 4-NO$_2$-phenyl | 6-Cl-3-pyridyl | H | CF$_3$ | H | H | 204–206 |
| I-16 | 6-Cl-3-pyridyl | 6-Cl-3-pyridyl | H | OCF$_3$ | H | H | 168–170 |
| I-17 | 4-F-phenyl | 6-Cl-3-pyridyl | H | CF$_3$ | CH$_3$ | H | 162–163 |
| I-18 | 4-F-phenyl | 6-Cl-3-pyridyl | H | OCF$_3$ | CH$_3$ | H | 126–127 |
| I-19 | 4-F-phenyl | 6-Cl-3-pyridyl | Cl | OCF$_3$ | CH$_3$ | H | 123–125 |
| I-20 | 4-Cl-phenyl | 6-Cl-3-pyridyl | H | CF$_3$ | CH$_3$ | H | 173–174 |
| I-21 | 4-Cl-phenyl | 6-Cl-3-pyridyl | H | SCF$_3$ | H | H | 188–189 |
| I-22 | 4-OCHF$_2$-phenyl | 6-Cl-3-pyridyl | H | OCF$_3$ | H | H | 182–185 |
| I-23 | 4-OCF$_3$-phenyl | 6-Cl-3-pyridyl | Cl | OCF$_3$ | H | H | 156–157 |
| I-24 | 4-Cl-phenyl | 6-Cl-3-pyridyl | Cl | OCF$_3$ | CH$_3$ | H | 138–140 |
| I-25 | 4-Cl-phenyl | 6-Cl-3-pyridyl | Cl | SCF$_3$ | CH$_3$ | H | 136–138 |
| I-26 | 4-Cl-phenyl | 6-Cl-3-pyridyl | H | OCF$_3$ | CH$_3$ | H | glassy |

EXAMPLE 3

(synthesis of starting compound)

(Compound No IV-7)

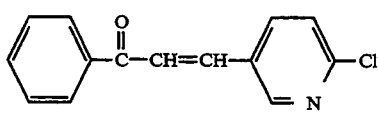

Acetophenone (12.0 g) and 6-chloro-nicotinic aldehyde (14.2 g) were dissolved in 100 ml of ethanol. To the resulting solution were dropwise added 20 ml of a 20% aqueous solution of sodium hydroxide at room temperature. The reaction mixture was stirred at room temperature for 1 hour. After that, the crystals thus formed were separated by filtration, washed with cold ethanol and dried in air to give 1-phenyl-3-(6-chloro-3-pyridyl)-propenone (19.9 g). mp 186°–189° C.

The 1-phenyl-3-(6-chloro-3-pyridyl)-propenone (2.44 g), which had been prepared in Example 3, was dissolved in 20 ml of ethanol. The resultant solution was admixed with 0.5 ml of hydrazine hydrate, and heated under reflux for 3 hours. After the completion of the reaction, the solvent was distilled off under reduced pressure to give 3-phenyl-5-(6-chloro-3-pyridyl)-2-pyrazoline (2.58 g).

$^1$H-NMR (90 MHz, δppm, CDCl$_3$) 2.98 (1H, dd)
3.53 (1H, dd)
4.93 (1H, dd)
6.00 (1H, m)
7.24–7.72 (7H, m)
8.33 (1H, d)

EXAMPLE 5

(synthesis of starting compound)

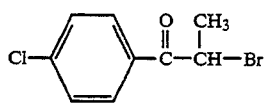

4'-chloropropiophenone (39.6 g) and anhydrous aluminum chlorid (0.1 g) were dissolved in 100 ml of chloroform. To the resulting solution was protionwise added bromine (37.6 g) at a temperature of 30° to 35° C. The reaction mixture was stirred at room temperature for 30 minutes. Then nitrogen was blown into the reaction mixture to remove the formed hydrogen bromide therefrom. Thereafter, the solvent was distilled off under reduced pressure to give 2-bromo-4'-chloropropiophenone (58.1 g). mp 77.5°–79.5° C.

EXAMPLE 6

(synthesis of starting compound)

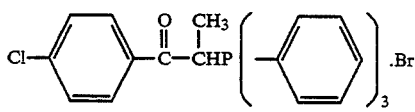

The 2-bromo-4'-chloropropiophenone (58.1 g), which had been prepared in Example 5, and triphenyl phosphine (61.6 g) were dissolved in 250 ml of acetonitrile. The resulting solution was heated under reflex for 1.5 hours. After the completion of the reaction, the reaction mixture was cooled with ice, and the crystalline material thus formed was separated by filtration, washed with cold acetonitrile and dried in air to give triphenyl[1-(4-chlorophenyl)-1-oxo-2-propyl]-phosphonium bromide (79.0 g). mp 258°–258.5° C.

EXAMPLE 7

(synthesis of starting compound)

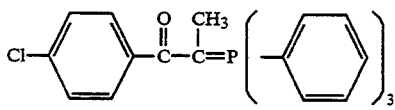

The triphenyl[1-(4-chlorophenyl)-1-oxo-2-propyl]-phosphonium bromide (10.2 g), which had been prepared in Example 6, was dissolved in 25 ml of methanol. To the resultant solution were added dropwise 5 ml of 30% aqueous solution of potassium hydroxide at room temperature. After the completion of the reaction, the reaction mixture was admixed with 150 ml of water, and crystalline material thus formed was separated by filtration and dried in air to give [1-(4-chlorophenyl)-1-oxo-2-propylidene]-triphenylphospholane (8.6 g). mp 179°–183.5° C.

EXAMPLE 8

(synthesis of starting compound)

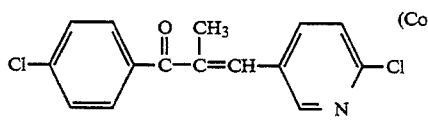
(Compound No IV-5)

The [1-(4-chlorophenyl)-1-oxo-2-propylidene]-triphenylphospholane (19.3 g), which had been prepared in Example 7, and 6-chloro-nicotinic aldehyde (6.4 g) were dissolved in 150 ml of toluene. The solution thus formed was heated under reflux for 5 hours. After the completion of the reaction, the solvent was distilled off under reduced pressure, and the crude product thus obtained was recrystallized from ethanol to give 1-(4-chlorophenyl)-2-methyl-3-(6-chloro-3-pyridyl)-2-propenone (9.5 g) mp 88° C.

EXAMPLE 9

(synthesis of intermediate compound)

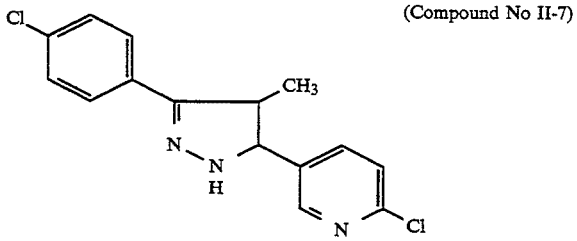
(Compound No II-7)

The 1-(4-chlorophenyl)-2-methyl-3-(6-chloro-3-pyridyl)-propenone (9.5 g), which had been prepared in Example 8, was dissolved in 60 ml of ethanol. The resultant solution was admixed with 5 ml of hydrazine hydrate, and heated under reflux for 3 hours. After the completion of the reaction, the solvent was distilled off under reduced pressure to give 3-(4-chlorophenyl)-4-methyl-5-(6-chloro-3-pyridyl)-2-pyrazoline (9.9 g) as oily substance.

The following Table 3 includes the compounds of Examples 4 and 9 along with others similarly produced:

TABLE 3 (II)

| No. | A | B | $R^1$ | $R^2$ | $^1$H-NMR (90 MHz, CDCl$_3$, ppm) |
|---|---|---|---|---|---|
| II-1 | 4-OCHF$_2$-phenyl | 6-Cl-3-pyridyl | H | H | 3.00 (1H, dd)<br>3.53 (1H, dd)<br>4.98 (1H, dd)<br>5.08 (1H, m)<br>6.52 (1H, t)<br>7.00–7.80 (6H, m)<br>8.37 (1H, d) |
| II-2 | 4-OCF$_3$-phenyl | 6-Cl-3-pyridyl | H | H | 2.95 (1H, dd) |

TABLE 3-continued

Structure (II):
A-C(=N-NH-)-CR¹(-CR²(B)-) (pyrazoline with A on C3, R¹ on C4, R² and B on C5)

| No. | A | B | R¹ | R² | ¹H-NMR (90 MHz, CDCl₃, ppm) |
|---|---|---|---|---|---|
| | | | | | 3.52 (1H, dd) |
| | | | | | 4.95 (1H, dd) |
| | | | | | 5.40 (1H, m) |
| | | | | | 7.10–7.36 (3H, m) |
| | | | | | 7.51–7.75 (3H, m) |
| | | | | | 8.33 (1H, d) |
| II-3 | 4-NO₂-phenyl | 6-Cl-3-pyridyl | H | H | 2.97 (1H, dd) |
| | | | | | 3.56 (1H, dd) |
| | | | | | 5.03 (1H, m) |
| | | | | | 6.33 (1H, m) |
| | | | | | 7.13–7.30 (6H, m) |
| | | | | | 8.33 (1H, dd) |
| II-4 | 4-(4-Br-phenoxy)-phenyl | 6-Cl-3-pyridyl | H | H | 2.95 (1H, dd) |
| | | | | | 3.55 (1H, dd) |
| | | | | | 4.97 (1H, dd) |
| | | | | | 5.83 (1H, m) |
| | | | | | 6.76–7.83 (10H, m) |
| | | | | | 8.37 (1H, dd) |
| II-5 | 4-OCH₃-phenyl | 6-Cl-3-pyridyl | H | H | oil |
| II-6 | 4-F-phenyl | 6-Cl-3-pyridyl | CH₃ | H | oil |
| II-7 | 4-Cl-phenyl | 6-Cl-3-pyridyl | CH₃ | H | oil |
| II-8 | phenyl | 6-Cl-3-pyridyl | H | H | 2.98 (1H, dd) |
| | | | | | 3.53 (1H, dd) |
| | | | | | 4.93 (1H, dd) |
| | | | | | 6.00 (1H, m) |
| | | | | | 7.34–7.72 (7H, m) |
| | | | | | 8.33 (1H, d) |
| II-9 | 4-Cl-phenyl | 6-Cl-3-pyridyl | H | H | 2.93 (1H, d) |
| | | | | | 3.50 (1H, dd) |
| | | | | | 4.96 (1H, dd) |
| | | | | | 5.20 (1H, m) |
| | | | | | 7.20–7.80 (6H, m) |
| | | | | | 8.33 (1H, d) |
| II-10 | 4-F-phenyl | 6-Cl-3-pyridyl | H | H | 2.90 (1H, dd) |
| | | | | | 3.50 (1H, dd) |
| | | | | | 4.95 (1H, m) |
| | | | | | 6.00 (1H, m) |
| | | | | | 6.87–7.83 (6H, m) |
| | | | | | 8.33 (1H, dd) |
| II-11 | 4-CH₃-phenyl | 6-Cl-3-pyridyl | H | H | 2.33 (3H, s) |
| | | | | | 2.90 (1H, dd) |
| | | | | | 3.50 (1H, dd) |
| | | | | | 4.86 (1H, dd) |
| | | | | | 5.67 (1H, dd) |
| | | | | | 7.07–7.60 (5H, m) |
| | | | | | 7.70 (1H, dd) |
| | | | | | 8.33 (1H, d) |
| II-12 | 4-tert-C₄H₅-phenyl | 6-Cl-pyridyl | H | H | 1.33 (9H, s) |
| | | | | | 2.98 (1H, dd) |
| | | | | | 3.53 (1H, dd) |
| | | | | | 4.93 (1H, dd) |
| | | | | | 6.00 (1H, m) |
| | | | | | 7.20–7.75 (6H, m) |
| | | | | | 8.33 (1H, d) |
| II-13 | 6-Cl-pyridyl | 6-Cl-pyridyl | H | H | 2.95 (1H, dd) |
| | | | | | 3.57 (1H, dd) |
| | | | | | 5.03 (1H, dd) |
| | | | | | 6.47 (1H, m) |
| | | | | | 7.30 (1H, d) |
| | | | | | 7.33 (1H, d) |
| | | | | | 7.97 (1H, dd) |
| | | | | | 8.35 (1H, d) |
| | | | | | 8.48 (1H, d) |
| II-14 | 6-Cl-pyridyl | 6-Cl-phenyl | H | H | 2.93 (1H, dd) |
| | | | | | 3.45 (1H, dd) |
| | | | | | 4.90 (1H, dd) |
| | | | | | 6.22 (1H, m) |
| | | | | | 7.20–7.35 (4H, m) |
| | | | | | 7.93 (1H, dd) |
| | | | | | 8.45 (1H, d) |
| II-15 | 3,4-Cl₂-phenyl | 6-Cl-pyridyl | H | H | oil |

The following Table 4 shows the compounds of Examples 3 and 8 along with others similarly produced:

TABLE 4

$$\underset{A-C-C=C-B}{\overset{O\ \ \ R^1\ R^2}{\|\ \ \ |\ \ \ |}} \quad (IV)$$

| No. | A | B | $R^1$ | $R^2$ | m.p. °C. |
|---|---|---|---|---|---|
| IV-1 | 4-OCHF$_2$-phenyl | 6-Cl-3-pyridyl | H | H | 157–589 |
| IV-2 | 4-OCF$_3$-phenyl | 6-Cl-3-pyridyl | H | H | 162–163 |
| IV-3 | 4-NO$_2$-phenyl | 6-Cl-3-pyridyl | H | H | 183–185 |
| IV-4 | 4-OCH$_3$-phenyl | 6-Cl-3-pyridyl | H | H | 148–151 |
| IV-5 | 4-Cl-phenyl | 6-Cl-3-pyridyl | CH$_3$ | H | 88 |
| IV-6 | 4-F-phenyl | 6-Cl-3-pyridyl | CH$_3$ | H | 77–78 |
| IV-7 | phenyl | 6-Cl-3-pyridyl | H | H | 186–189 |
| IV-8 | 4-F-phenyl | 6-Cl-3-pyridyl | H | H | 152–154 |
| IV-9 | 4-Cl-phenyl | 6-Cl-3-pyridyl | H | H | 173–175 |
| IV-10 | 4-CH$_3$-phenyl | 6-Cl-3-pyridyl | H | H | 180–182 |
| IV-11 | 4-tert-C$_4$H$_5$-phenyl | 6-Cl-3-pyridyl | H | H | 165–166 |
| IV-12 | 3,4-Cl$_2$-phenyl | 6-Cl-3-pyridyl | H | H | 122–123 |
| IV-13 | 6-Cl-3-pyridyl | 6-Cl-3-pyridyl | H | H | 227–228 |
| IV-14 | 6-Cl-3-pyridyl | 4-Cl-phenyl | H | H | 168–169 |

Biotest Example

Comparative Compounds

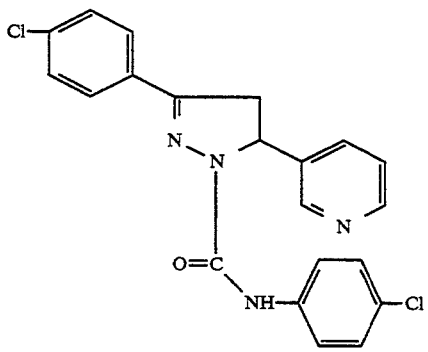

C-1

(disclosed in Japanese Laid-open Patent Application No. 87028/1973)

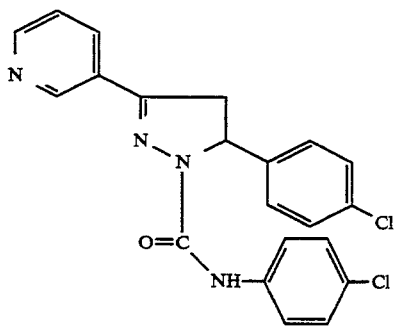

C-2

(also disclosed in Japanese Laid-open Patent Application No. 87028/1973)

Test Example 1

Biotest carried out against larvae of *Spodoptera litura*

Preparation of test formulation:
solvent: 3 parts by weight of xylene
Emulsifier: 1 part by weight of polyoxyethylene-alkylphenyl-ether To prepare suitable formulations of the active compounds, 1 part by weight of each of the active compounds was mixed with the above-mentioned amount of the emulsifier, and the mixture was diluted with water to the predetermined concentration.

Test Method

Leaves of sweet potato plants (lpomoea batatas Lam.) were soaked in a diluent aqueous solution of an active compound having a predetermined concentration, dried in air and placed on a dish with a diameter of 9 cm. 10 pieces of 3-instar larvae of *Spodoptera litura* were released into the dish, which was then placed in a greenhouse having a constant temperature of 28° C. After 7 days, the number of killed insects was determined to obtain the mortality of the insects.

The results are shown in Table 5.

TABLE 5

| Compound No. | Concentration of active compound (ppm) | Insect mortality after 7 days (%) |
|---|---|---|
| 1 | 40 | 100 |
| 6 | 40 | 100 |
| 7 | 40 | 100 |
| 8 | 40 | 100 |
| 9 | 40 | 100 |
| 11 | 40 | 100 |
| 12 | 40 | 100 |
| 13 | 40 | 100 |
| 14 | 40 | 100 |
| 22 | 40 | 100 |
| Control | | |
| C-1 | 1000 | 0 |
| C-2 | 1000 | 0 |

What is claimed is:
1. A pyrazoline of the formula

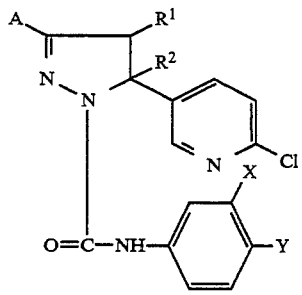

(I)

wherein $R^1$ and $R^2$ represent hydrogen, $C_{1-4}$ alkyl, or unsubstituted or halogen-substituted phenyl, A represents phenyl which may be substituted by at least one substituent selected from the group consisting of halogen, $C_{1-4}$ alkyl, $C_{1-4}$ alkoxy, halogeno-$C_{1-4}$ alkyl, halogeno-$C_{1-4}$ alkoxy, nitro, haloalkylenedioxy, unsubstituted or halogen-substituted phenyl, and unsubstituted or halogen-substituted phenoxy, or A represents halogen-substituted 3-pyridyl, X and Y individually represent hydrogen, halogen, $C_{1-4}$ alkyl, halogeno-$C_{1-4}$ alkyl, halogeno-$C_{1-4}$ alkoxy or halogeno-$C_{1-4}$ alkylthio, or X and Y together form a haloalkylenedioxy group, with the proviso (a) that X and Y do not simultaneously represent hydrogen, and with the further proviso (b) that, when $R^1$ and $R^2$ simultaneously represent hydrogen, then (i) A represents phenyl substituted by at least one substituent selected from the group consisting of halogeno-$C_{1-4}$ alkoxy, nitro, halomethylenedioxy, unsubstituted or halogen-substituted phenyl and unsubstituted or halogen-substituted phenoxy, or (ii) at least one of X and Y represents halogeno-$C_{1-4}$ alkoxy or halogeno-$C_{1-4}$ alkylthio, or (iii) X and Y together form a haloalkylenedioxy group.

2. A compound according to claim 1, wherein $R^1$ and $R^2$ represent hydrogen, methyl, ethyl, isopropyl, tert-butyl or unsubstituted or chlorine-substituted phenyl, A represents phenyl which may be substituted by at least one member selected from the group consisting of fluorine, chlorine, bromine, $C_{1-4}$ alkyl, $C_{1-2}$ alkoxy, fluoro- and/or chloro-$C_{1-2}$ alkyl, fluoro- and/or chloro-$C_{1-2}$ alkoxy, nitro, difluoromethylenedioxy, unsubstituted or fluoro- and/or chloro-substituted phenyl, and unsubstituted or chloro- and/or bromo-substituted phenoxy, or A represents fluoro, chloro- or bromo-substituted 3-pyridyl, X and Y represent hydrogen, chlorine, fluoro- and/or chloro-$C_{1-2}$ alkyl, fluoro- and/or chloro-$C_{1-2}$ alkoxy, or fluoro-and/or chloro-$C_{1-2}$ alkylthio, or X and Y together form a difluoromethylenedioxy or a tetrafluoroethylenedioxy group, with the proviso (a) that X and Y do not simultaneously represent hydrogen, and with the (b) further proviso that, when $R^1$ and $R^2$ simultaneously represent hydrogen atom, then (i) A represents phenyl substituted by at least one substituent selected from the class consisting of fluoro- and/or chloro-$C_{1-2}$ alkoxy, nitro, difluoromethylenedioxy, unsubstituted or fluoro- and/or chloro-substituted phenyl and unsubstituted or chloro- and/or bromo-substituted phenoxy, or (ii) one of X and Y represents fluoro-and/or chloro-$C_{1-2}$ alkoxy or fluoro and/or chloro-$C_{1-2}$ alkoxy or fluoro- and/or chloro-$C_{1-2}$ alkylthio, or (iii) X and Y together form difluoromethylenedioxy or tetrafluoroethylenedioxy.

3. A compound according to claim 1 wherein $R^1$ and $R^2$ represent hydrogen, methyl, ethyl, isopropyl, tert-butyl, phenyl, 4-chlorophenyl, A represents phenyl which may be substituted by at least one group selected from the class consisting of fluorine, chlorine, methyl, tert-butyl, methoxy, trifluormethyl, difluoromethoxy, trifluoromethoxy, nitro, difluoromethylenedioxy, unsubstituted or chloro-substituted phenyl, and unsubstituted or chloro- and/or bromo-substituted phenoxy, or A represents chlorine- or bromine-substituted 3-pyridyl, X represents hydrogen or chlorine and Y represents chlorine, difluoromethyl, trifluoromethyl, trifluoromethoxy or trifluoromethythio, or X and Y together form a difluoromethylenedioxy group or a tetrafluoroethylenedioxy group, and with the proviso (b) that, when $R^1$ and $R^2$ simultaneously represent a hydrogen atom, then (i) A represents phenyl, which may be substituted by at least one group selected from the group consisting of difluoromethoxy, trifluoromethoxy, nitro, difluoromethylenedioxy, unsubstituted or chloro-substituted phenyl and unsubstituted or chloro- and/or bromo-substituted phenoxy, or (ii) Y represents trifluoromethoxy or trifluoromethythio, or (iii) X and Y together form a difluoromethylenedioxy group or a tetrafluoroethylenedioxy group.

4. A compound according to claim 1, wherein such compound is 1-(4-trifluoromethyoxyphenyl) carbamoyl-3-phenyl-5-(6-chloro-3-pyridyl)-2-pyrazoline of the formula

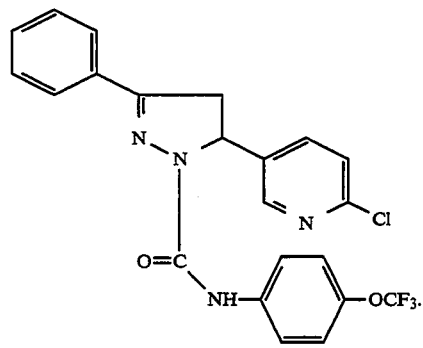

5. A compound according to claim 1, wherein such compound is 1-(4-trifluoromethylphenyl) carbamoyl-3-(4 chlorophenyl)-4-methyl-5-(6-chloro-3-pyridyl)-2-pyrazoline of the formula

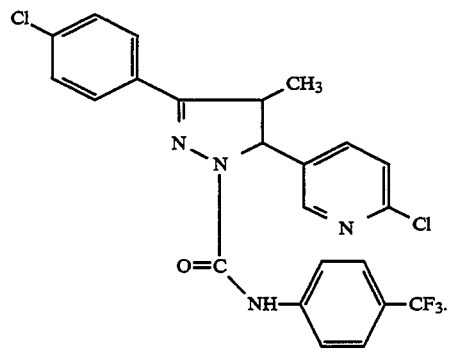

6. An insecticidal composition comprising an insecticidally effective amount of a compound according to claim 1 and a diluent.

7. A method of combating insects which comprises applying to such insects or to a locus from which it is desired to exclude such insects, an insecticidally effective amount of a compound according to claim 1.

8. The method according to claim 7, wherein such compound is 1-(4-trifluoromethoxyphenyl) carbamoyl-3-phenyl-5-(6-chloro-3-pyridyl)-2-pyrazoline or 1-(4-trifluoromethylphenyl) carbamoyl-3-(4-chlorophenyl)-4-methyl-5-(6-chloro-3-pyridyl)-2-pyrazoline.

* * * * *

UNITED STATES PATENT AND TRADEMARK OFFICE
CERTIFICATE OF CORRECTION

PATENT NO. : 5,389,648
DATED : February 14, 1995
INVENTOR(S) : Tsuboi, et al.

It is certified that error appears in the above-indentified patent and that said Letters Patent is hereby corrected as shown below:

Col. 22, line 57    After " pyridyl, " insert -- and --

Col. 23, line 18    After " pyridyl, " insert -- and --

Col. 23, line 43    Delete " trifluormethyl " and substitute -- trifluoromethyl --

Col. 24, lines 3-4  Delete " trifluoromethythio " and substitute -- trifluoromethylthio --

Col. 24, line 8     Delete " trifluoromethyoxyphenyl " and substitute -- trifluoromethoxyphenyl --

Signed and Sealed this

Twenty-fifth Day of April, 1995

Attest:

BRUCE LEHMAN

*Attesting Officer*   *Commissioner of Patents and Trademarks*